United States Patent [19]

Reinicke

[11] Patent Number: 4,604,090
[45] Date of Patent: Aug. 5, 1986

[54] COMPACT IMPLANTABLE MEDICATION INFUSION DEVICE

[75] Inventor: Robert H. Reinicke, Mission Viejo, Calif.

[73] Assignee: Consolidated Controls Corporation, El Segundo, Calif.

[21] Appl. No.: 554,197

[22] Filed: Nov. 22, 1983

[51] Int. Cl.⁴ ............................................. A61M 1/00
[52] U.S. Cl. ........................... 604/118; 128/DIG. 12; 604/122; 604/131
[58] Field of Search ............... 604/49, 131, 132, 140, 604/141, 151, 152, 153, 118, 122, 891, 65–67, 245–246; 128/DIG. 12, DIG. 13, 419 P

[56] References Cited

U.S. PATENT DOCUMENTS

| | | | |
|---|---|---|---|
| 3,527,220 | 9/1970 | Summers | 604/153 |
| 3,692,027 | 9/1972 | Ellinwood, Jr. | 604/891 |
| 3,923,060 | 12/1975 | Ellinwood, Jr. | 128/DIG. 13 |
| 3,951,147 | 4/1976 | Tucker et al. | 604/891 |
| 3,963,380 | 6/1976 | Thomas, Jr. et al. | 128/1 D |
| 4,013,074 | 3/1977 | Siposs | 604/891 |
| 4,077,405 | 3/1978 | Haerten et al. | 128/DIG. 13 |
| 4,146,029 | 3/1979 | Ellinwood, Jr. | 128/419 P |
| 4,152,098 | 5/1979 | Moody et al. | 604/153 |
| 4,191,181 | 3/1980 | Franetzki et al. | 128/DIG. 12 |
| 4,265,241 | 5/1981 | Portner et al. | 604/131 |
| 4,360,019 | 11/1982 | Portner et al. | 604/151 |
| 4,373,527 | 2/1983 | Fischell | 128/DIG. 13 |
| 4,395,259 | 7/1983 | Prestele et al. | 604/67 |
| 4,431,425 | 2/1984 | Thompson et al. | 604/246 |
| 4,443,218 | 4/1984 | De Cant, Jr. et al. | 604/67 |
| 4,464,178 | 8/1984 | Dalton | 604/174 |
| 4,486,190 | 12/1984 | Reinicke | 604/67 |
| 4,525,165 | 6/1985 | Fishnell | 604/131 |

FOREIGN PATENT DOCUMENTS

WO84/01718 5/1984 PCT Int'l Appl. ............. 604/131

Primary Examiner—C. Fred Rosenbaum
Assistant Examiner—Gene B. Kartchner
Attorney, Agent, or Firm—Mason, Kolehmainen, Rathburn & Wyss

[57] ABSTRACT

An implantable medication infusion device wherein a generally cylindrical manifold is employed having a shallow recess on one face thereof. A flexible diaphragm is positioned to form with the face of said manifold a medication reservoir. A circular cover member is positioned over the diaphragm to form with said diaphragm a pressure stabilizing chamber within which is positioned a two-phase fluid for maintaining a constant pressure on said diaphragm. A permanent magnet is positioned at the center of said diaphragm and is movable therewith. A Hall effect transducer positioned on said manifold opposite said permanent magnet is employed continuously to measure the position of said diaphragm and provide an indication of the amount of medication in said reservoir.

A method of filling and sealing the pressure stabilizing chamber which insures that a small bubble of two-phase fluid is present in said chamber at all times.

An inlet filter is positioned between the medication reservoir and an inlet check valve to act as a bubble trap during the intake stroke of a pulsatile pumping unit also mounted in the manifold.

22 Claims, 15 Drawing Figures

U.S. Patent  Aug. 5, 1986  Sheet 1 of 4  4,604,090
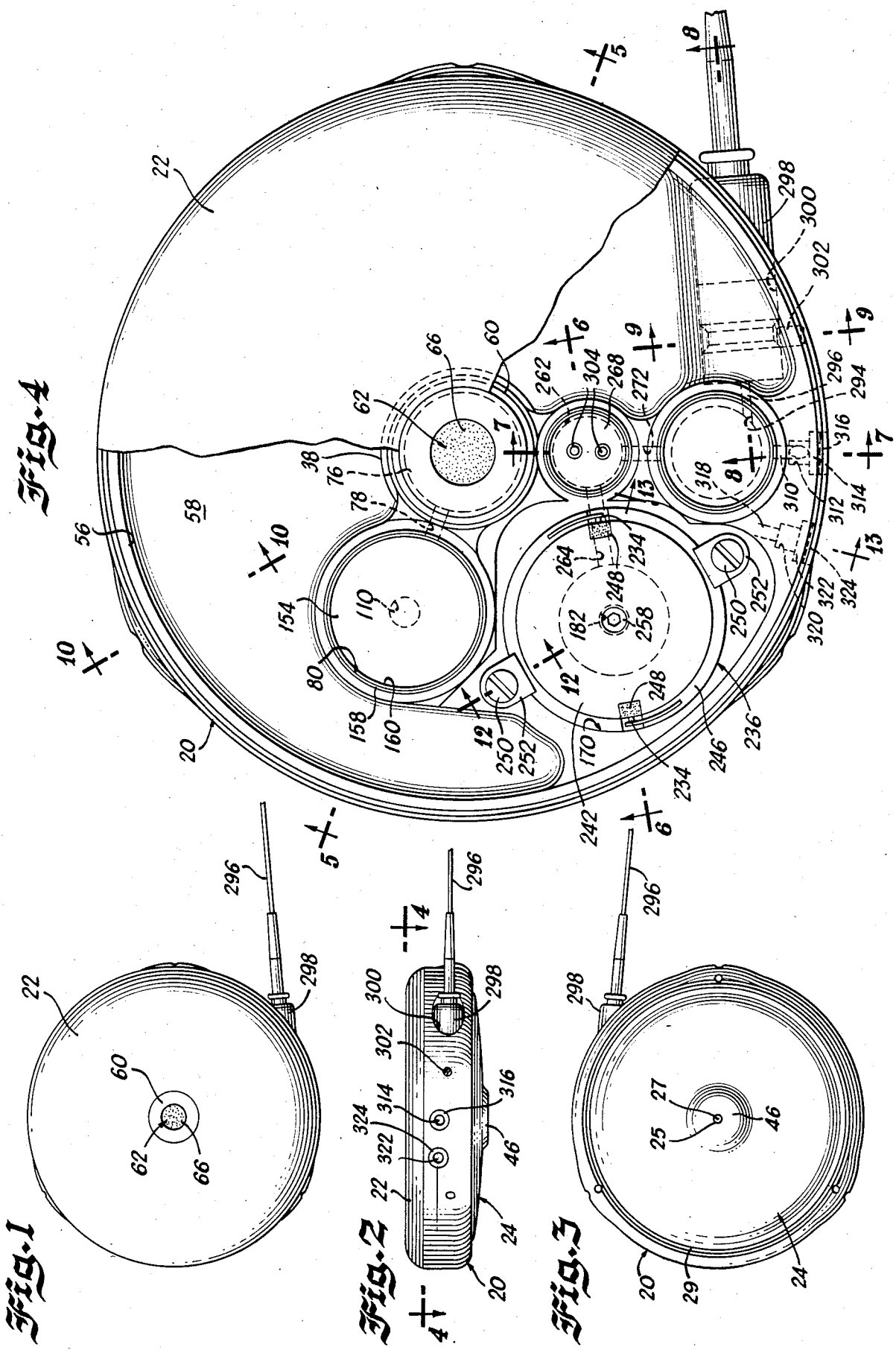

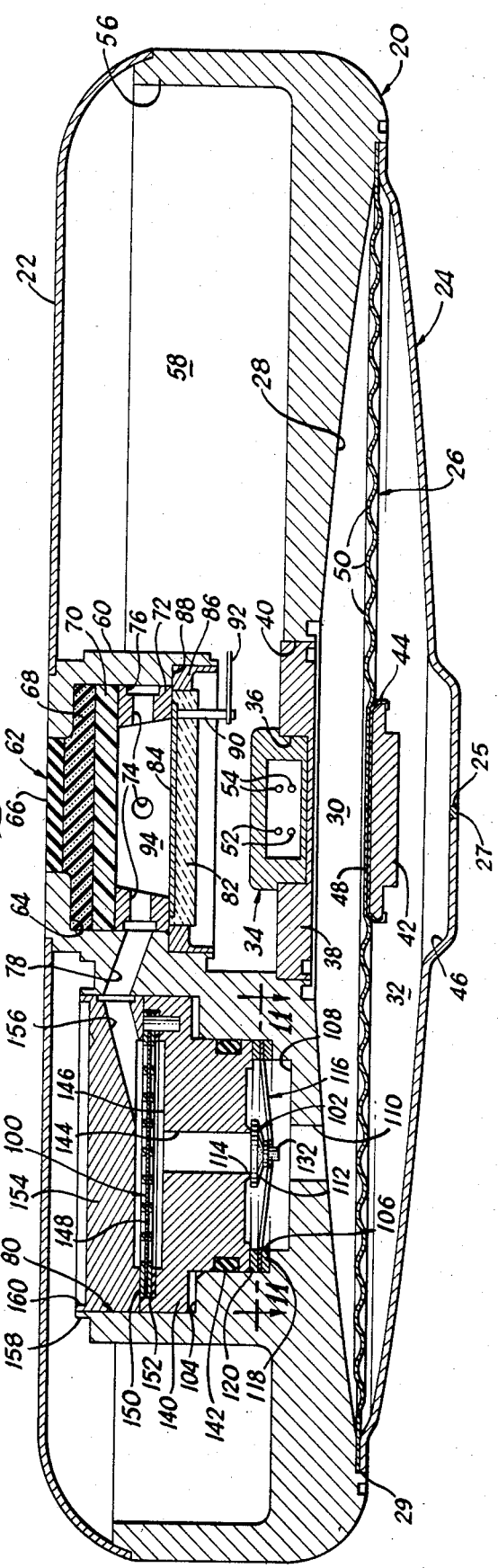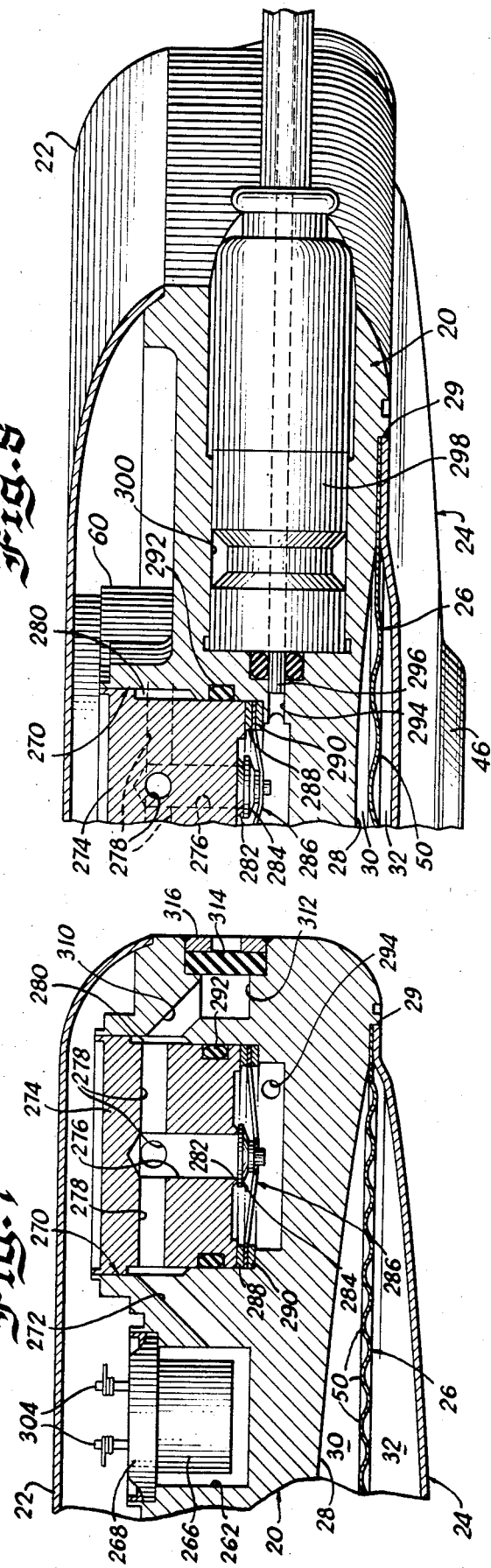

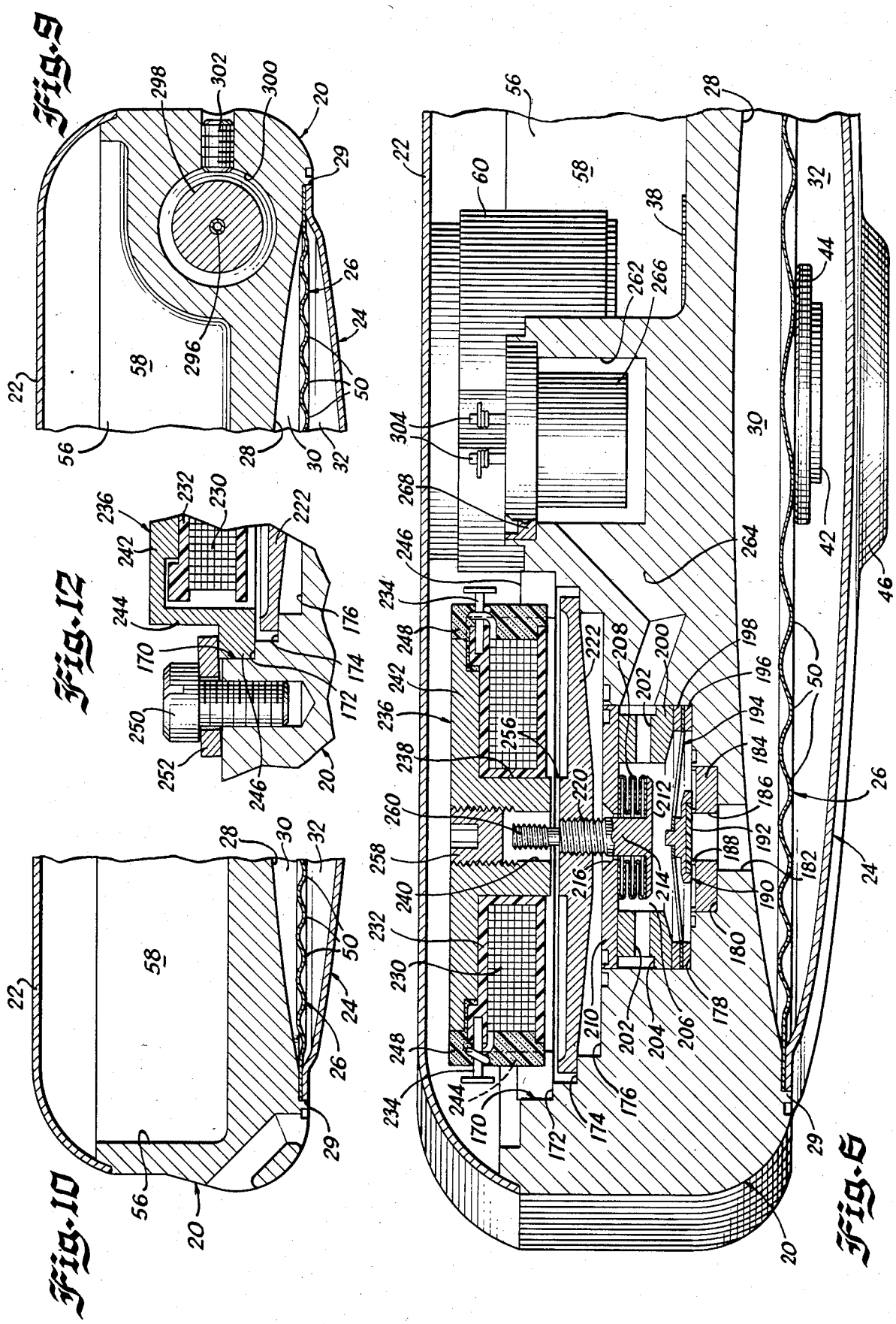

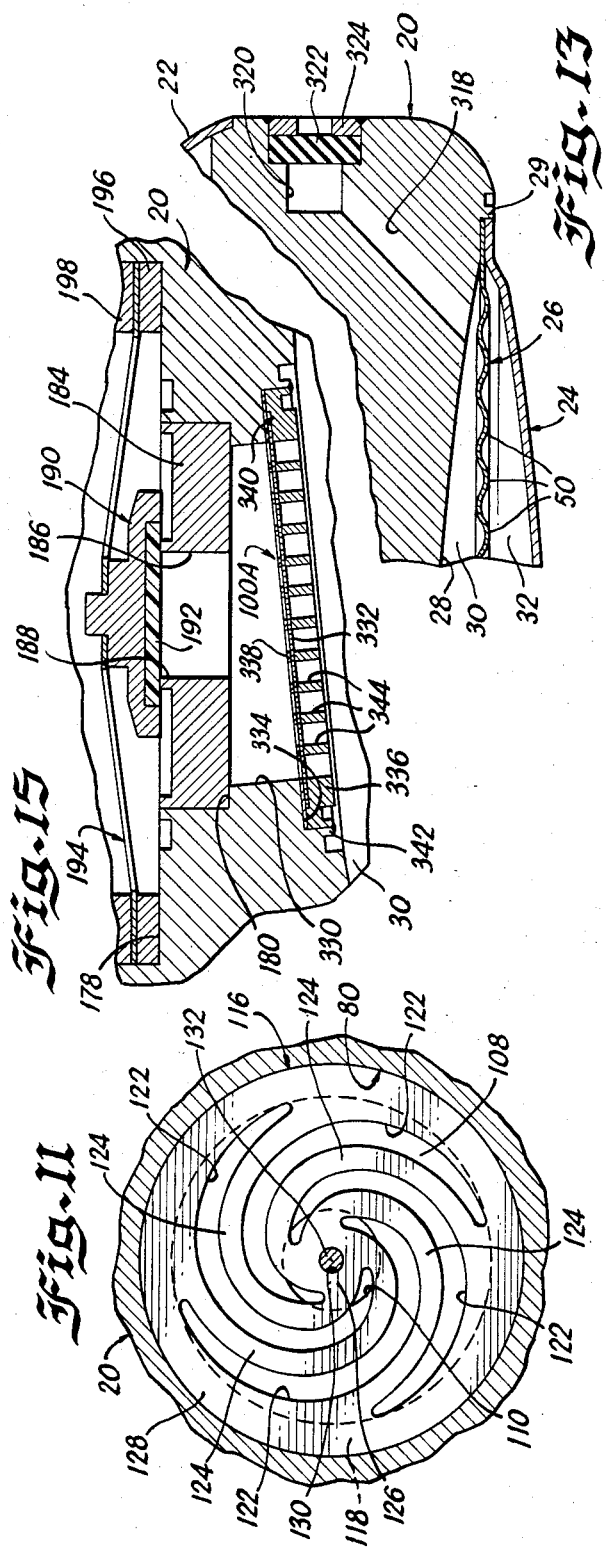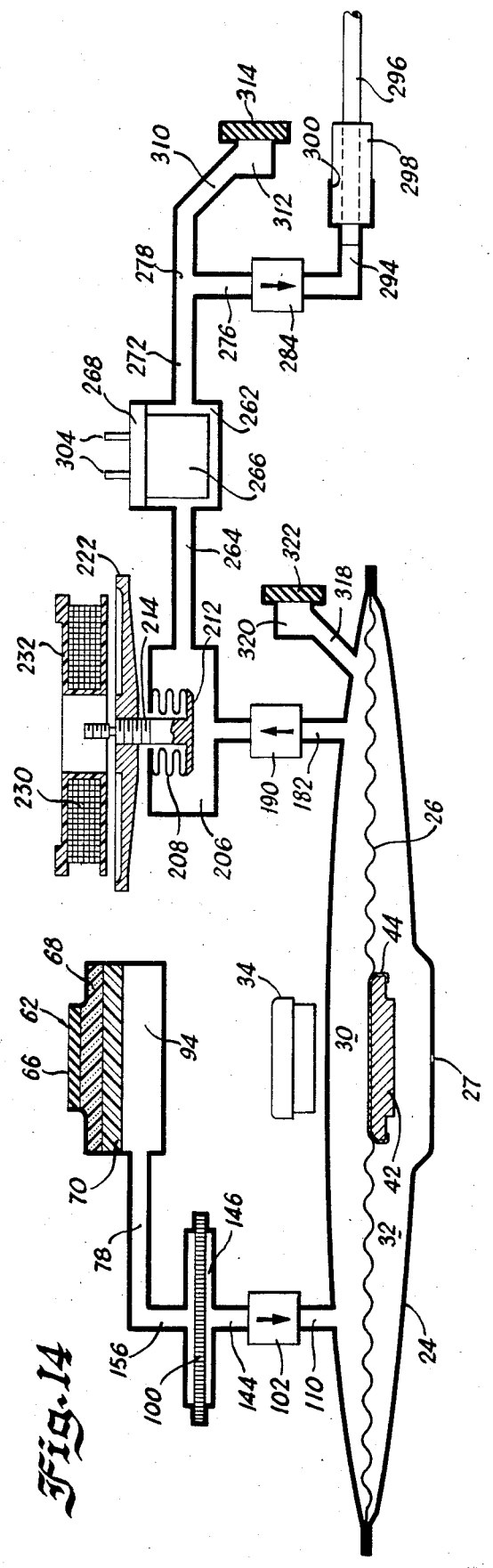

COMPACT IMPLANTABLE MEDICATION INFUSION DEVICE

The present invention relates to implantable medication infusion devices, and more particularly to implantable medication infusion devices of the so-called pulsatile type wherein medication is dispensed to the body during short dispensing periods separated by relatively long intervals between dispensing periods.

Many implantable devices in the prior art have employed so-called pulsatile medication dispensing arrangements. Examples of such pulsatile dispensing systems are shown in Summers Pat. No. 3,527,220; Ellinwood Pat. No. 3,692,027; Ellinwood Pat. No. 3,923,060; Thomas et al Pat. No. 3,963,380; Haerten et al Pat. No. 4,077,405; Ellinwood Pat. No. 4,146,029; Moody Pat. No. 4,152,098; Franetzki et al Pat. No. 4,191,181; Portner Pat. No. 4,265,241; Dorman International Publication No. WO81/00209; and Fischell Pat. No. 4,373,527.

Some of these pulsatile systems have used inlet and outlet check valves in connection with a pumping chamber with the pump element acting to withdraw a metered amount of medication from a reservoir during the intake stroke of the pump and dispensing this metered amount of medication to an output catheter during the return stroke of the pump element. In such arrangements, the outlet check valve closes and the inlet check valve opens on the intake stroke of the pump so that medication can be drawn from the reservoir into the pumping chamber. In other pulsatile systems, an outlet flow restriction has been employed instead of an outlet check valve, for example, in Haerten et al Pat. No. 4,077,405. In such devices compliance of the pumping chamber prevents the accurate dispensing of a fixed amount of medication for each stroke of the pump, because the pressure head across the pump will vary with different operating conditions. Variations of the pressure head across the pump will produce corresponding variations in the bolus, i.e., the volume of medication forced through the restrictor during the medication dispensing period. Such variations in pressure head can occur due to changes in altitude and temperature of the person carrying this kind of device, since the pressure within the body, i.e., the pressure at the outlet of the flow restrictor, varies with changes in altitude, and the pressure at the pump inlet varies with changes in temperature of the medication reservoir. In my copending application Ser. No. 453,594, filed Dec. 27, 1982, now Pat. No. 4,486,190, a precision medication dispensing system and method is disclosed whereby a programmed time average rate of infusion of medication into the body is precisely maintained throughout all operating temperature and pressure conditions.

In the Ellinwood and Fischell patents, identified above, various types of programmable arrangements are employed to control the flow of medication to the body in accordance with a predetermined medication programming system. In such arrangements it is desirable to have continuously available a measure of the amount of medication remaining in the reservoir of the implantable device. In the Fischell patent mentioned above a pressure switch arrangement is employed to indicate when the pressure in the reservoir chamber reaches a predetermined level, this pressure switch being used during the filling procedure to indicate by a telemetering system when the amount of medication in the reservoir has reached the specific value. However, other than providing an indication when a maximum filling pressure has been reached, the Fischell arrangement provides no indication of the medication remaining in the reservoir as the medication is dispensed to the body during succeeding days and weeks. In Haerton Pat. No. 4,077,405 an arrangement similar to the Fischell patent is provided wherein a pressure sensor is positioned in the pressure regulating chamber which is used to provide a constant pressure on the medication reservoir. The pressure sensor is employed to compensate for changes in the temperature of pressure caused by fever, or the like, but does not provide an indication of the amount of medication in the reservoir.

In addition to the above mentioned defects, the prior implantable medication dispensing units have been quite bulky, hard to manufacture and difficult to assemble on a mass production basis. One of the difficulties involved in producing a commercially acceptable implantable medication infusion unit is that all of the air must be evacuated from the system to prepare it for use. The system is then filled with water first, without introducing air, and the water is then replaced with a suitable medication solution, such as insulin, or the like. In those implantable systems employing fill check valves and check valves on either side of a pulsatile pumping unit it is not possible to evacuate all of the air from the system simply by placing evacuation needles in the input and output of the unit. This is because the series connected check valves will close at a predetermined low pressure and retain a small amount of air between the two series connected check valves.

A further problem can arise in implantable medication infusion devices of the pulsatile pump type due to bubbles in the medication flowing to the pumping chamber. The pumping efficiency will be reduced due to the high compliance of such bubbles and if enough bubble volume is introduced the pump could cease to function completely. Bubbles can be introduced into the reservoir during refill due to incomplete purging of bubbles from the refill system external to the implanted device. Also, if an improperly vacuum conditioned medication is used bubbles can form in the reservoir under certain conditions.

It is an object, therefore, of the present invention to provide a new and improved implantable medication infusion unit which avoids one or more of the above discussed difficulties of prior art arrangements.

It is another object of the present invention to provide a new and improved implantable medication infusion unit wherein indicating means capable of providing on command a signal corresponding to the amount of medication in the medication reservoir of the implantable unit is provided.

It is a further object of the present invention to provide a new and improved implantable medication infusion unit wherein indicating means of minimal dimensions are incorporated in a compact implantable unit and provide on command a signal corresponding to the amount of medication in the medication reservoir of the implantable unit.

It is another object of the present invention to provide a new and improved implantable medication infusion unit which can be readily and completely evacuated prior to filling the unit with water or medication.

It is still another object of the present invention to provide a new and improved medication infusion unit which is extremely compact, can be readily manufactured on a mass production basis, and is capable of being assembled and filled in a simple, safe and reliable manner.

It is a further object of the present invention to provide a new and improved method of filling and sealing the pressure stabilizing portion of an implantable medication infusion device.

It is another object of the present invention to provide a new and improved implantable medication infusion device wherein bubbles in the medication reservoir of the implantable device are prevented from reaching the pumping chamber of the implantable device.

It is still another object of the present invention to provide a new and improved implantable medication infusion device of the pulsatile pump type wherein filter means are provided between the medication reservoir and the pumping chamber which permits a predetermined small amount of medication to be admitted to the pumping chamber during the intake stroke of the pump while preventing the flow of bubbles into said pumping chamber from the medication reservoir.

The invention both as to its organization and method of operation, together with further objects and advantages thereof, will best be understood by reference to the following specification taken in connection with the accompanying drawings, in which:

FIG. 1 is a top elevational view of an implantable medication infusion unit according to the present invention;

FIG. 2 is a side elevational view of the unit of FIG. 1;

FIG. 3 is a bottom elevational view of the unit of FIG. 1;

FIG. 4 is a sectional view taken along the line 4—4 of FIG. 2 with the cover of the unit partially broken away;

FIG. 5 is a sectional view taken along the line 5—5 of FIG. 4;

FIG. 6 is a sectional view taken along the line 6—6 of FIG. 4;

FIG. 7 is a sectional view taken along the line 7—7 of FIG. 4;

FIG. 8 is a sectional view taken along the line 8—8 of FIG. 4;

FIG. 9 is a sectional view taken along the line 9—9 of FIG. 4;

FIG. 10 is a sectional view taken along the line 10—10 of FIG. 4;

FIG. 11 is a sectional view taken along the line 11—11 of FIG. 5;

FIG. 12 is a sectional view taken along the line 12—12 of FIG. 4;

FIG. 13 is a sectional view taken along the line 13—13 of FIG. 4;

FIG. 14 is a simplified diagram illustrating how the main components of the unit of FIG. 1 are interconnected; and FIG. 15 is a fragmentary sectional view of an alternative embodiment of the invention which is similar to FIG. 6 and illustrates the placement of the inlet filter between the reservoir and the inlet check valve.

Referring now to the drawings, the implantable medication infusion unit of the present invention is therein illustrated as comprising a flat disk like manifold indicated generally at 20, made of cast, machined and/or sheet metal titanium, to which is secured a top cover 22 and a bottom cover 24 to provide a totally enclosed and sealed unit which may be conveniently implanted within the body. A flexible diaphragm indicated generally at 26 is secured at its outer edge between the edge of the bottom cover 24 and the manifold 20. The bottom surface of the manifold 20 is scalloped to provide a shallow recess 28 which together with the diaphragm 26 forms a medication reservoir 30 which may be filled with a desired medication in a manner to be described in more detail hereinafter.

The space between the diaphragm 26 and the bottom cover 24 provides a pressure stabilizing chamber 32 which is filled with a fluid which through a change of state establishes a substantially constant pressure on the medication within the reservoir 30 despite changes in the volume of medication within the reservoir 30 and changes in temperature and pressure within the body. For example, the fluid sealed within the chamber 32 may be a two-phase mixture of Freon 112 and Freon 113 to provide a medication reservoir pressure that is always less than body pressure. This fluid is placed within the chamber 32 in accordance with a filling procedure described in more detail hereinafter.

In accordance with an important aspect of the present invention, means are provided for measuring the distance between the diaphragm 26 and the central portion of the manifold 20 and producing, upon command, an electrical signal corresponding to such measurement. Since the separation between the diaphragm 26 and the manifold 20 can be calibrated in terms of the volume of liquid within the chamber 30, this signal can provide at any time a measure of the amount of medication remaining in the reservoir 30. More particularly, a Hall effect transducer 34 is positioned within a recess 36 in a titanium insert 38 which is positioned within a central opening 40 in the manifold 20. Preferably, the insert 38 is secured to the manifold 20 by a tungsten inert gas (TIG) welding of the lip portions adjacent the opening 40 by a meltdown welding process in which no additional metal is added. A permanent magnet 42, which is preferably of samarium cobalt, is held against the underside of the diaphragm 26 by means of a titanium sheet metal cup 44, the cup being resistance welded to diaphragm 26 and crimped over magnet 42 to hold the magnet firmly to the diaphragm. The diaphragm 26 is provided with the central flat portion 48 against which the magnet cup 44 is welded and against which the magnet 42 rests, the remainder of the diaphragm 26 having the corrugations 50 so as to provide a flexible diaphragm which can move sufficiently to conform to either the curved outer cover 24 or the curved face 28 of the manifold 20 when the volume of the reservoir 30 goes from maximum to minimum values. The magnet 42 is located by being secured within the magnet cup 44. Preferably the diaphragm 26 is made of one mil thick titanium.

The Hall effect transducer 34 is provided with the input terminals 52, to which an energizing voltage is supplied when it is desired to measure the medication within the reservoir 30, and output terminals 54 across which is developed the Hall effect output signal which is proportional to the field strength of the magnet 42 and hence the position of the diaphragm 26 relative to the transducer 34. The manifold 20 is provided with an upstanding wall portion 56 around a substantial portion of its periphery which defines, together with the top cover 22 the chamber 58 within which the electronic circuits of the implanted unit, which may be either discrete or integrated, are positioned. Considering generally, these elements will usually comprise a source of energy, such as a lithium battery, capacitor charging and discharging circuits for developing energizing pulses for the solenoid operated pump to be described in more detail hereinafter, and various additional circuitry necessary to control the programmed operation of this pump. In addition, the chamber 58 includes suitable circuitry for supplying an energizing signal to the input terminals 52 of the Hall effect transducer 34 and for receiving the output signal developed on the output terminals 54 thereof and processing this signal in any suitable manner to provide the desired indication of the amount of medication in the reservoir 30. Preferably, the Hall affect transducer 34 is not continuously energized, but instead is signalled upon command by the electronics within the chamber 58, in order to conserve the energy consumed by the implantable unit.

In accordance with an important aspect of the invention, the above described mixture is inserted and sealed into the chamber 32 before the bottom cover 24 is secured to the manifold 20. More particularly, after the components 42, 44 are secured to the diaphragm 26, the edge of the diaphragm 26 is welded to the periphery of the cover 24 while this cover is still unattached to the manifold 20 to form a pressure chamber subassembly 24, 26. This pressure chamber subassembly is then clamped to a fixture which simulates the curved surface 28 of the manifold 20 so that a simulated reservoir 30 is formed between the diaphragm 26 and this fixture. A small central opening 25 is provided in the bottom cover 24 through which the Freon mixture is inserted. Since this mixture is preferably at a pressure below body pressure, it is necessary to follow special procedures to preclude the introduction of air into chamber 32 and to assure that a small Freon mixture bubble exists at all times in chamber 32, even when the reservoir is completely full, i.e. when the volume of chamber 32 is minimum. The Freon 112 and 113 are first mixed in proportions of about 25 percent and 75 percent, by weight, respectively, to achieve a vapor pressure of approximately 8–9 psia at body temperature, i.e. a vapor pressure that maintains the reservoir pressure below body pressure up to 10,000 feet altitude and up to 104° F. body temperature. This mixture is then vacuum conditioned to remove most absorbed air. The Freon mixture and the simulated reservoir-pressure chamber subassembly are heated to 125° F. After a vacuum is pulled in chamber 32 and in the simulated reservoir 30 in the fixture, the heated Freon mixture is introduced into both of these chambers so that initially there is no pressure differential across the diaphragm 26. A 10 psig nitrogen (or air) gas pressure is then applied through the fixture to the medication side of diaphragm 26 which expels most of the Freon mixture within the chamber 32 out the hole 25 and firmly positions the diaphragm 26 against the cover 24. However, a small amount of Freon mixture remains in the chamber 32 between the corrugations 50 of the diaphragm 26 and the cover 24. A plug 27 is resistance welded into hole 25 while being submerged in the expelled Freon mixture to prevent the introduction of air into the chamber 32. The 10 psig nitrogen gas pressure is then removed and the pressure chamber subassembly 24, 26 cools to room temperature, thus causing the "mechanical" volume of chamber 32 to increase slightly due to some springback of the diaphragm 26, and also causing the fluid volume of the Freon mixture to reduce slightly, due to the bulk temperature coefficient. The total of these two volume changes cause a small Freon mixture vapor bubble to be formed in chamber 32 that is equal in size to this total volume change. This vapor bubble acts as a site to initiate immediate and proper vaporization of the liquid Freon mixture as medication is removed from chamber 30 and the diaphragm 26 moves away from the cover 24. Without this initial nucleation site, it has been found that the Freon mixture, under certain conditions, can fail to vaporize and the diaphragm 26 does not move away from the curved surface of the cover 24 to maintain the pressure constant within the reservoir 30. After the chamber 32 has been filled and sealed with the Freon mixture the pressure chamber subassembly 24, 26 is removed from the fixture and the cover 24 with diaphragm 26 attached is welded to the manifold by TIG melt down welding of the lip portion 29 with the associated outer edge of the cover 24.

In order to fill the reservoir 30 with medication, the manifold 20 is provided with a central portion 60 which is positioned above the Hall affect transducer 34 in the manner illustrated in FIG. 5 and a penetrable septum indicated generally at 62 is seated against the shoulder portion 64 formed in the central portion 60 of the manifold 20. More particularly, the septum 62 comprises an upper layer 66 of silicon rubber, an intermediate layer 68 of silicon rubber with a graphite filler so that it is electrically conductive, this layer being pressed against the shoulder 64, and a bottom layer 70 of butyl rubber. The silicone layers self seal the syringe needle penetrations while the bottom layer 70 of butyl rubber is employed to reduce gas permeability through the septum 62. A teflon spacer ring 72 is positioned in engagement with the periphery of the bottom layer 70 of the septum 62, the ring 72 being provided with a plurality of radially outwardly directed openings 74 which communicate with an annular passageway 76 formed in the periphery of the ring 72. Passageway 76 communicates with the passageway 78 formed in the manifold 20, the passageway 78 in turn communicating with a top opening recess 80 formed in the manifold 20.

A ceramic disk 82, on the upper surface on which is provided a metalized layer 84, is fused to a titanium ring 86 which is seated on the shoulder portion 88 formed in the portion 60 of the manifold 20. A pin 90 which is electrically connected to the conductive layer 84, extends through the ceramic disk 82 and a wire 92 is connected to the bottom end of the pin 90. When tne titanium ring 86 is seated on the shoulder 88 it urges the Teflon ring 72 and hence the conductive layer 68 of the septum 62 against the shoulder 68 so that this conductive layer is electrically connected to the titanium manifold 20. Accordingly, when a conductive needle is inserted through the three layers of the penetrable septum 62 and strikes the conductive layer 84 the resistance between the wire 92 and the manifold 20 is reduced markedly due to the short circuiting effect of the conductive needle. This change in resistance is detected by any suitable circuit arrangement within the chamber 58 to determine that the needle has been inserted through the septum 62 to the proper depth to position its open end within the central chamber 94 formed by the Teflon ring 72. Upon receipt of this signal by telemetry the refill operation can proceed with safety.

In assembly, the penetrable septum 62, the teflon ring 72 and titanium insert 86 are first assembled within the portion 60 of the manifold 20 through the central opening 40 of the manifold 20 and before the insert 38 supporting the Hall effect transducer 34 is inserted. The insert 86 is then TIG meltdown welded to the adjacent lip portion 60 after which the titanium insert 38 carrying the Hall effect transducer 34 is positioned in the manifold 20 and welded thereto.

Within the recess 80 there is provided an inlet filter indicated generally at 100 and a fill check valve indicated generally at 102. The recess 80 is provided with a series of steps 104, 106 and 108 of progressively smaller diameter and communicates at the bottom portion thereof with the reservoir 30 through the passageway 110. The fill check valve 102 comprises a movable valve element 112 which is normally urged against a fixed annular valve seat 114 by a flexible support member 116. The outer edge of the support member 116 is positioned between a pair of shims 118 and 120, the bottommost shim 118 resting on the shoulder 106 of the recess 80 in the manifold 20. The thickness of the shims 118, 120 may be selected so as to bias the movable valve element 112 against the valve seat 114 with a desired cracking pressure.

Preferably, the supporting member 116 is provided with a plurality of arcuate cut out portions 122 (FIG. 11) which define a series of arcuate spring arms 124 connecting the central portion 126 of the member 116 with the outer periphery 128 thereof. A central opening 130 is provided in the member 116 for receiving and locating the downwardly extending portion 132 of the movable valve element 112. By employing the arcuate cut out portions 122 in the member 116 the supporting flexible arms 124 are of sufficient length to provide the necessary flexibility and travel for movable valve element 112 within the relatively small dimensions of the bottom portion of the recess 80. Preferably the movable valve element 112 is biased so that it will open at a filling pressure of 13 p.s.i.

A titanium insert 140 is seated on the upper shim 120 and is provided with the O-ring seal 142, the insert 140 having a central passage 144 in the bottom edge of which is formed the fixed valve seat 114. The filter 100 is seated in the insert 140 and communicates with the passageway 144 through the top opening 146 in the insert 140. The filter 100 comprises a cellulose acetate sheet 148, preferably of 1.2 micron rating, which is supported by and positioned between a pair of supporting plates 150 and 152 which have a large number of holes for accommodating flow of medication through the sheet 148. An upper titanium insert 154 is seated on the insert 140 and holds the filter 100 in place, the insert 154 being provided with the passage 156 in communication with the passageways 78 in the manifold 20 and having an opening corresponding to the opening 146 in the insert 140 for access to the filter 100. After all of the above described components have been inserted into the recess 80 the upper insert 154 is sealed to the manifold 20 by a TIG melt down welding process of the lip portions 158 and 160, in the manner described heretofore in connection with the insert 40.

Considering now the manner in which the pulsatile pumping unit is mounted in the manifold 20, a top opening recess 170 in the manifold 20 is provided with a series of shoulders 172, 174, 176, 178 and 180 of progressively smaller diameter, the recess 170 communicating with the reservoir 30 through the passageway 182. Titanium insert 184 is seated on the shoulder 180 and is secured to the manifold 20 by TIG meld down welding of the adjacent lip portions of the insert 184 and manifold 20. The insert 184 is provided with a central opening 186 in the upper edge of which is formed a fixed valve seat 188 and a movable valve element 190 carries a silicon elastomer insert 192 which is normally seated on the valve seat 188. The inlet valve member 190 is seated on and urged against the fixed valve seat 188 by means of the support member 194 which may be of similar construction to the support member 116 described in detail heretofore. The member 194 is positioned between the pair of spacer shims 196 and 198 which are seated on the shoulder 178 and are of the correct thickness to provide the desired biasing pressure for the inlet check valve element 190. Preferably the inlet check valve element 190 is set to open at two p.s.i. A titanium ring 200 is seated on the upper shim 198 and is provided with a plurality of radially extending passages 202 which communicate with an annular passage 204 in the periphery of the ring 200. The space within the ring 200 and down to the insert 184 forms a pumping chamber 206 into which medication may be drawn through the passages 182 and 186 from the reservoir 30 when the pump is actuated.

The pulsatile pumping element comprises a bellows 208 which is secured between a top plate 210 and the lower flange 212 provided on the bottom of an upstanding post 214 which extends through a clearance opening 216 in the plate 210. After the elements of the inlet check valve 190 are assembled on the shoulder 178 and the ring 200 and top plate 210 are positioned on top of the shim 198, the plate 210 is secured to the manifold 20 by TIG melt down welding of the adjacent lip portions thereof. The post 214 is provided with a threaded portion 220 which receives the threaded central opening of a flat disk armature 222 the outer edge of which rests on the shoulder 174. Preferably the armature 222 is of soft ferromagnetic material such as core iron or 430F stainless steel.

In order to actuate the pumping unit a solenoid coil 230 is wound on the coil form 232 with the terminals 234 thereof extending from opposite sides of the coil form in the top wall thereof. The coil form 232 is mounted in a housing 236 of magnetic material. This housing has a central core portion 238 provided with the opening 240 therein, a top wall portion 242, and an outer wall 244 which terminates in an outerwardly extending flange 246 which rests on the shoulder 172 of the manifold 20. The housing 236 is provided with diametrically opposed slots in the walls 244 which receive the terminals 234 and are then filled with a suitable potting compound 248. The outer flange 246 of the housing 236 is secured against the shoulder 172 by means of the screws 250 (FIG. 4) and retaining plates 252 which engage the edge of the flange 246. Preferably, the solenoid coil 230 comprises 97 turns of insulated copper wire AWG No. 28.

In assembling the solenoid pumping unit after the plate 210 has been welded to the manifold 20, the armature is threaded onto the threaded portion 220 of the post 214 until it rests on the shoulder 174. Continued rotation of the armature lifts the post 214 upward and places a preload on the bellows 208. Normally this preload is 0.6 pounds. After the desired preload has been established for the bellows 208, the housing 236 with the solenoid coil 230 assembled therein is mounted on the shoulder 172 and secured in place by the screws 250. In this connection it will be noted that the gap between the outer edge of the armature 222 and the flange portion 246 of the housing 236 is smaller than the gap 256 between the armature 222 and the central core 238 of the housing 236. This provides a small gap between armature 222 and central core 238 when the solenoid is in its energized position and the outer edge of the armature 222 engages the flange 246. Upon removal of the electrical energizing voltage, this gap ensures a higher and more repeatible drop-out current.

After the housing 236 has been clamped in place the threaded cap 258 may be removed from the central opening 240 in the housing 236 and a measuring instrument connected to the threaded upper end 260 of the post 214. This measuring device can measure the preload established by the bellows 208. Also by exerting an upward pull on the stem 260 the pull exerted until the armature 222 strikes the flange 246 may be measured as well as the maximum travel of the armature 222. Also the spring rate characteristic of the bellows 208 as it is compressed may be measured.

In operation, when the solenoid coil 230 is energized by a pulse from the electronic circuitry in the chamber 58, the armature 220 is attracted upwardly against the bottom face of the outer flange 246 of the housing 236 so that the bellows 208 is compressed and the volume within the pumping chamber 206 is abruptly increased. The inlet valve element 190 is not connected to the head portion 212 of the post 214. However, as soon as the pressure within the pumping chamber 206 is reduced under 2 p.s.i. below the medication pressure in the reservoir, the inlet valve 190 opens and admits fluid from the reservoir 30 into the pumping chamber 206. The inlet check valve 190 returns to its initial closed position after a volume of medication equal to that of the compression of the bellows 208 (typically 1 microliter) flows into the pumping chamber 206 and increases the pumping chamber pressure to reduce the pressure differential across the inlet check valve 190 to its reseat value.

It should be noted that the motion of the small solenoid operated bellows 208 and the inlet check valve 190 during the intake stroke of the solenoid actuated pump, are quite fast. For example, the upward motion of the bellows 208 when the coil 230 is energized will take typically on the order of 0.0005 seconds. The inlet check valve 190 will follow this upward movement of the bellows and then takes a substantially longer time, in the order 0.005 seconds to settle back onto the seat 188 as fluid flows into the chamber 206 and increases the pumping chamber pressure.

Following closure of the inlet check valve 190, the solenoid coil 230 is deenergized and the mechanical spring force of the compressed bellows 208, acting on the effective area of the head portion 212, increases the pumping chamber pressure above body pressure. In this connection it will be noted that the inlet check valve 190 is not restricted in its movement to the upward movement of the bellows 208 since the inlet check valve 190 is separated from the head portion 212 by a substantial distance. Accordingly, it is not necessary for the inlet check valve to have a diameter as great or greater than the effective diameter of the bellows 208. This is because the volume displaced by upward movement of the bellows 208 may be accommodated by greater upward motion of the inlet check valve 190. When a preloading force is exerted on the inlet check valve by engagement with the bellows directly, as described in my copending application Ser. No. 453,594, now U.S. Pat. No. 4,486,190, the inlet check valve must have a diameter at least as great as the effective diameter of the bellows. However, with the arrangement shown in FIG. 6 such a large diameter inlet check valve is not required. However, it is important to locate the check valve very close to the bellows and without any fluid restriction (such as a small passage) to avoid cavitation during the intake stroke.

The pumping chamber 206 communicates with a top opening recess 262 in the manifold 20 through the passage ways 202 and 204 in the ring 200 and a passageway 264 in the manifold 20. A pressure transducer 266 is positioned in the recess 262 and is arranged to measure the pressure within the pumping chamber 206. The pressure transducer 266 is preferably mounted on a titanium insert 268 which is secured within the recess 262 by TIG melt down welding of the adjacent lips of the insert 268 and the manifold 20. The recess 262 also communicates with a top opening recess 270 (FIG. 7) in the manifold 20 through the passage 272. A titanium insert 274 is positioned within the recess 270 and is provided with a central opening 276 which is connected through a plurality of radially extending passageways 278 with a peripheral passageway 280 in communication with the passageway 272. A fixed outlet check valve seat 282 is formed in the bottom end of the passage 276 and the movable valve element 284 of this outlet check valve is supported on the valve seat 282 by the member 286 which is positioned between the spacer shims 288 and 290. The member 86 preferably has a construction similar to the supporting member 1 and 4 described in detail heretofore. An O-ring 292 provided in the wall of the insert 274 is provided to seal this insert within the recess 270 and the insert is secured to manifold 20 by TIG melt down welding of the adjacent lip portions thereof after the shims 288, 290, the support member 286 and movable valve element 284, and the insert 274 have been inserted into the recess 270. Preferably the outlet check valve element 284 is set to open at a pressure of 13 p.s.i. in a manner similar to the inlet check valve element 112 described in detail heretofore.

A passageway 294 is provided in the sidewall of the recess 270 below the outlet check valve 284 and is adapted to receive the inlet 296 of a catheter assembly 298 which is positioned in an opening 300 in the manifold 20 which extends to the exterior of the manifold, the catheter assembly 298 being retained in position within the opening 300 by means of a set screw 302 (FIG. 9). When the pressure within the pumping chamber 206 increases above body pressure, medication is forced out through the conduit 264, the recess 262, the conduit 272 and the outlet check valve 284 to the catheter assembly 298 so that it can be dispensed to any desired location within the body, as will be readily understood by those skilled in the art.

The pressure transducer 266 is used for general monitoring of the operation of the implanted unit and can be employed to verify that each pulse supplied to the solenoid coil 230 actually produces a change in pressure within the pumping chamber 206. To this end, the terminals 304 of the pressure transducer 266 may be connected to any suitable counting circuit which may then be compared with the pulse producing circuit in the electronic circuitry in the chamber 58. In addition, the pressure transducer 266 may be employed to observe the waveform of the pumping pressure transient produced within the pumping chamber 206 to check on the operation of the bellows 208 and to determine generally how the pump is functioning. In this connection it should be understood that the manifold 20 is arranged so that it may function with the type of solenoid pump and pumping pressure transient measurement and feedback arrangement described in my copending application Ser. No. 453,594, now U.S. Pat. No. 4,486,190, it being only necessary to substitute a flow restriction device in the recess 270 in place of the outlet check valve 282, 284, as will be readily understood by those skilled in the art. In such instance the pressure transducer 266 would measure the pumping pressure transient for each actuation of the solenoid coil and the output of this pressure transducer would be integrated and employed to control the timing of pulses supplied to the solenoid coil, in the manner described in detail in said copending application.

In FIG. 14 the main components of the system described thus far are shown diagrammatically with the same reference numerals as applied in the preceding detailed description. It will be seen by reference to FIG. 14 that the fill check valve 102, the inlet check valve 190 and the outlet check valve 284 are all connected in series and operate in the same direction. In order to prepare the implantable unit for implantation in the body, it is necessary first to evacuate the entire system to remove all air therefrom after which the system is first filled with water and then the water filling is replaced by the desired medication. However, when two or more check valves are connected in series, as for example, the combination 102, 190, or the combination 190, 284 in FIG. 14, it is not possible to evacuate the entire system by simply inserting suitable evacuation needles into the inlet and outlet ports of the device. This is because one or more of the check valves will close when the pressure in the system falls below its closing pressure and will trap air between the two series connected check valves.

In accordance with a further aspect of the present invention evacuation ports are provided between each set of series connected check valves so that the space between each pair of check valves may be evacuated at the same time that the remainder of the system is evacuated. More particularly, the portion of the system from the inlet check valve 190 through the pumping chamber 206 and through the passageways and recesses connected to the outlet check valve 284 may all be evacuated through a port 310 (FIG. 7) which communicates with a chamber 312 within which is positioned a penetrable septum 314, this septum being held in position within the chamber 312 by the titanium insert 316 suitably welded to the manifold 20. In a similar manner the portion of the system between the fill check valve 102 and the inlet check valve 190, i.e. tne space below the fill valve seat 114, the passageway 110, the reservoir 30 and the passageways 182 and 186, may all be evacuated through a port 318 (FIG. 13) in the manifold 20 which extends from the reservoir 30 to a chamber 320 which is accessible from the exterior through a penetrable septum 322 held in place by the titanium insert 324 which is welded to the manifold 20. Accordingly, in the arrangement of the present invention needles are simultaneously inserted through septums 62, 314 and 322 and suitable evacuation apparatus is connected to the catheter assembly 298 and a vacuum is simultaneously pulled through all four of these points so as to remove all air from the system. Then, through suitable valving, water is inserted through these needles and fills the entire assembly. After all air has been removed from the implantable unit and water fills the entire system, the unit may be transported or stored awaiting implant in the body. Just prior to implantation the water may be replaced by the desired medication by supplying medication through the entry septum 62 while continuously operating the solenoid actuated pump so that the water in the entire system is replaced by medication.

The fill check valve 102 provides a seal that is redundant to the septum 62 and operates to prevent leakage of body fluids past a leaky septum 62 into the reservoir 30. However, under certain conditions it can be desirable, or even quite necessary, to remove residual medication from the unit if a different potency or type of medication is to be used. Also, in the case of medications, such as insulin, which tend to deteriorate, precipitate and/or loose potency due to prolonged storage at body temperature, it is desirable to remove any residual medication before refilling the reservoir with fresh medication. Under these conditions, the fill check valve 102 is preferably eliminated so as to allow residual medication in the reservoir to be removed by means of a syringe needle which is extended through the septum 62 and is employed to withdraw any residual medication from the reservoir 30 and the passageways interconnecting this reservoir with the chamber 94, prior to refilling of the reservoir. When the fill check valve 102 is not employed it then becomes unnecessary to provide the evacuation port 318 and septum 322 since the inlet chamber 94, passageways 78, 156, 144 and 110, and the reservoir 30 may all be evacuated through the septum 62 when the fill check valve 102 is eliminated.

In FIG. 15 an alternative embodiment of the invention is shown wherein the inlet filter 100 is positioned between the reservoir 30 and the inlet check valve 190. When the inlet filter is positioned in this location it serves as a "bubble trap" as well as a particulate and bacteria filter that prevents any bubbles and particulates from passing through the inlet check valve into the pumping chamber 206. If bubbles happen to enter the pumping chamber 206 which are not subsequently absorbed into the medication the pump efficiency will be reduced due to the high compliance of the bubbles and, if enough bubble volume is introduced, the pump can become totally disabled. Thus, a prefered position of the inlet filter 100 is as shown in FIG. 15 if bubbles exist in the reservoir 30. Bubbles can be introduced into this reservoir by several means. First, bubbles can inadvertently be introduced into the reservoir during the refilling operation due to an incomplete purging of bubbles from the refill system external to the implanted device. Secondly, if an improperly vacuum conditioned medication is used and the medication is supersaturated at body temperature and reservoir pressure, dissolved gases could come out of solution and form bubbles in the reservoir 30. Thirdly, gases that are normally dissolved in body fluids, such as carbon dioxide, could permeate through the septum 62 and form bubbles in the reservoir 30, in the event that an fill check valve 102 is not employed. The first and third above described situations should normally be prevented by using vacuum-conditioned (de-gased) medication. However, if the medication is not vacuum conditioned properly then the bubbles would not be absorbed. In all cases bubbles would be eventually absorbed into the reservoir medication, given the proper use of vacuum conditioned medication during subsequent refills of the reservoir.

Referring now to FIG. 15, wherein the same reference numerals have been given for elements common to FIG. 6, the inlet filter 100A is positioned in a passageway 330 in the manifold 20 which is of relatively large diameter as compared to the passageway 186 in FIG. 6, the filter 100A being positioned immediately beneath the insert 184 on which the inlet check valve 190 is seated. The inlet filter 100A comprises a thin, flexible filter disc 332, which may either be of woven wire mesh or a porous membrane, which is positioned in a shallow top recess 340 in a rigid, relatively thick titanium support member 336. A thin back up plate 338 of titanium, preferably having a thickness of 0.002 inches, is positioned over the filter disc 332 and is welded along its outer edge to the support 336 to form a subassembly in which the filter disc 332 is retained between the support 336 and the back up plate 338. This subassembly is seated on the shoulder 340 formed in the manifold 20 and the titanium support 338 is then welded to the adjoining lip 342 formed in the manifold 20. Both the back up plate 338 and the support 336 are provided with relatively large openings 344 which permit unimpeded flow of the medication fluid to and through the filter disc 332.

If the inlet filter 100A is positioned at the location shown in FIG. 15 and functions in a conventional manner, medication would have to flow through the filter 100A during the pump intake stroke which lasts for only about one quarter of a millisecond. However, such operation would not be satisfactory since the very high instantaneous flow rate of 4,000 microliters per second, assuming a pump intake of 1 microliter per stroke, would cause an excessive filter pressure drop thus causing the release of dissolved gases and/or cavitation in the pumping chamber. In accordance with an important aspect of the present invention such high instantaneous flow rate is avoided by designing the filter disc 332 and back up plate 338 so that they are flexible enough to deflect slightly during the pump intake stroke. This deflection displaces one microliter of medication with a filter pressure drop of less than ½ p.s.i.d. The filter disc 332 and back up plate 338 return back to their normal position as medication passes through the filter during the time period between pump actuations. Since under normal rates of dispensation for medication such as insulin the time period between pump dispensing periods is at least one minute, the flow rate to transport one microliter through the filter 100A is extremely low and the filter will operate well even if it starts to become clogged with particles. Thus, deflection of the filter elements 332 and 338 permits 1 microliter of filtered medication to pass into the pumping chamber 206 without requiring a high flow rate of medication through the filter itself.

When the inlet filter 100A is made sufficiently flexible that it deflects sufficiently to displace one microliter of medication during the pump intake stroke a filter pressure drop of less than ½ p.s.i.d. is produced across the inlet filter 100A which is insufficient to permit bubbles to be transmitted through the filter. Depending upon tne exact type of membrane or wire mesh filter disc 332, a bubble requires from one to at least three p.s.i.d. to pass through the filter element, i.e. the so called "bubble point" of the filter. Since the filter pressure drop during the pump intake stroke is less than ½ p.s.i.d. a bubble will not be able to pass through the filter 100A as long as the outlet side of the filter is wetted with medication. This bubble-blocking phenomenon is due to the surface tension forces of the medication at the bubble-to-medication interfaces at the filter pores. In this connection it will be understood that various sizes of inlet filters 100A may be employed depending upon the type of medication used. An example of a woven wire screen is a wire mesh of double dutch twilled weave having a wire count of 325×2300 and a micron rating of 15 microns. Porous membranes having a micron range of from 0.22 to 5.0 microns may also be employed as the filter element 332. In this connection it will be understood that a deflection of less than 0.001 inches in the filter disc 332 and backup plate 338 is sufficient to displace one microliter of medication.

Although the present invention has been described with reference to the illustrated embodiments thereof, it should be understood that numerous other modifications and embodiments can be made by those skilled in the art that will fall within the spirit and scope of the principles of this invention.

What is claimed as new and desired to be secured by Letters Patent of the United States is:

1. An implantable medication infusion unit, comprising a flat generally disc shaped manifold having a shallow recess on one face thereof, a flexible circular diaphragm secured at its periphery to the edge of said recess to form with said one face of said manifold a medication reservoir, means accessible from the exterior of said unit through a first penetrable septum mounted in the other face of said manifold for filling said medication reservoir, said last named means including a fill check valve, a pulsatile pumping unit mounted in said manifold and including an inlet check valve mounted in said manifold, a second penetrable septum mounted in said manifold, means defining a chamber beneath said second penetrable septum, and a passage in said manifold interconnecting said chamber and said reservoir, whereby the space between said fill check valve and said inlet check valve may be evacuated through said penetrable second septum.

2. An implantable medication infusion unit, comprising a flat generally disc shaped manifold having a shallow recess on one face thereof, a flexible circular diaphragm secured at its periphery to the edge of said recess to form with said one face of said manifold a medication reservoir, a pulsatile pumping unit mounted in said manifold and including an inlet check valve mounted in said manifold and connected to said medication reservoir, said pulsatile pumping unit also having an outlet check valve mounted in said manifold, a penetrable septum mounted in said manifold, means defining a chamber beneath said septum, and passage means in said manifold interconnecting said chamber with the space between said inlet check valve and said outlet check valve, whereby said space may be evacuated through said penetrable septum.

3. An implantable medication infusion unit, comprising a flat generally disc shaped manifold having a shallow recess on one face thereof, a flexible circular diaphragm secured at its periphery to the edge of said recess to form with said one face of said manifold a medication reservoir, means defining a pumping chamber in said manifold, an inlet check valve between said medication reservoir and said pumping chamber, a catheter assembly mounted in said manifold and extending to the exterior of said unit, an outlet check valve between said pumping chamber and said catheter assembly, a penetrable septum mounted in said manifold, means defining a chamber beneath said septum, and passage means in said manifold interconnecting said chamber and said pumping chamber so that said pumping chamber may be evacuated through said penetrable septum.

4. In an implantable medication infusion device of the type which includes a pressure stabilizing chamber formed by a flexible member and an opposed rigid cover member, the method of filling and sealing said pressure stabilizing chamber which comprises the steps of heating said chamber and a two-phase fluid to an elevated temperature, introducing said heated fluid into said chamber, forcing said flexible member against said cover to expel heated fluid through an opening in said cover, sealing said opening while it is submerged in heated fluid expelled from said chamber, and removing said force from said flexible member and cooling said chamber so that a small vapor bubble is formed in said chamber due to the increase in volume of said chamber produced by said removal of force and said cooling, said vapor bubble acting as a site to facilitate vaporization of said fluid as said flexible member is moved away from said cover.

5. The method of claim 4 wherein said elevated temperature is just below the boiling point of said two-phase fluid.

6. The method of claim 4 wherein said two-phase fluid is a mixture of 25% Freon 112 and 75% Freon 113, by weight.

7. The method of claim 4, wherein said two-phase fluid has a vapor pressure of approximately 8.5 psia at body temperature.

8. The method of claim 7, wherein said mixture is heated to a temperature of 125° F.

9. The method of filling and sealing the pressure stabilizing chamber subassembly of an implantable medication infusion device, said device including a generally cylindrical manifold having a shallow recess on one face thereof, said pressure stabilizing chamber subassembly being formed by a flexible diaphragm secured to a cover member which subassembly is adapted to be secured to said manifold so that said diaphragm forms with said face of said manifold a medication reservoir, which comprises the steps of filling said pressure stabilizing chamber with a two-phase fluid which is heated to a temperature just below the boiling point thereof, forcing said diaphragm against said cover member to expel heated fluid through an opening in said cover, sealing said opening while it is submerged in heated fluid expelled from said chamber, and removing said force from said diaphragm and cooling said chamber so that a small vapor bubble is formed in said chamber due to the increase in volume of said chamber produced by said removal of force and said cooling, said vapor bubble acting as a site to facilitate vaporization of said fluid as said diaphragm is moved away from said cover.

10. The method of claim 9 which includes the step of securing said cover member to said manifold after said vapor bubble is formed in said pressure stabilizing chamber.

11. The method of claim 9 which includes the step of securing said subassembly to a fixture having a shallow recess in one face thereof which simulates said shallow recess in said manifold to form a simulated medication reservoir between said diaphragm and said fixture, and filling both said pressure stabilizing chamber and said simulated medication reservoir with said heated two phase liquid.

12. The method of claim 11, which includes the step of evacuating both said pressure stabilizing chamber and said simulated medication reservoir before said two-phase fluid is placed therein.

13. The method of claim 11, which includes the step of supplying gas under pressure through said fixture to the medication reservoir side of said diaphragm, thereby forcing said diaphragm against said cover member and expelling said heated fluid through said opening.

14. The method of claim 13, which includes the step of securing said cover member to said manifold after said vapor bubble is formed in said pressure stabilizing chamber.

15. In an implantable medication infusion unit, the combination of, a medication reservoir, a pumping chamber, a pulsatile pumping unit connected to a movable wall portion of said pumping chamber and adapted to increase the volume of said pumping chamber during the intake stroke thereof, an inlet check valve positioned between said reservoir and said pumping chamber and arranged to open during the intake stroke of said pumping unit, and filter means positioned between said reservoir and said inlet check valve, said filter means including a filter element which flexes toward said inlet check valve during the intake stroke of said pumping unit to permit a predetermined amount of medication which has already passed through said filter element to flow through said inlet check valve into said pumping chamber, wherein said filter element comprises a thin back up plate of titanium having relatively large openings therein, and a porous membrane positioned adjacent said back up plate, both said back up plate and said porous membrane being sufficiently flexible to permit said predetermined amount of medication to flow through said inlet check valve into said pumping chamber.

16. The combination of claim 15, wherein said porous membrane has a filter rating of from 0.22 to 5.0 microns.

17. In an implantable medication infusion unit, the combination of, a medication reservoir, a pumping chamber, a pulsatile pumping unit connected to a movable wall portion of said pumping chamber and adapted to increase the volume of said pumping chamber during the intake stroke thereof, an inlet check valve positioned between said reservoir and said pumping chamber and arranged to open during the intake stroke of said pumping unit, and filter means positioned between said reservoir and said inlet check valve, said filter means including a filter element which flexes toward said inlet check valve during the intake stroke of said pumping unit to permit a predetermined amount of medication which has already passed through said filter element to flow through said inlet check valve into said pumping chamber, the increase in volume of the pumping chamber being greater than the volume of flow through said filter during the pump stroke, the amount of flex being proportional to the difference between the increase in volume of the pumping chamber and the volume of flow through the filter during the pump stroke and selected to limit the pressure drop across the filter to a level insufficient to permit bubbles to be generated.

18. The combination of claim 17, wherein medication passes through said filter element from said reservoir during the periods between the intake strokes of said pumping unit.

19. In an implantable medication infusion unit, the combination of, a medication reservoir, a pumping chamber, a pulsatile pumping unit connected to a movable wall portion of said pumping chamber and adapted to increase the volume of said pumping chamber during the intake stroke thereof, an inlet check valve positioned between said reservoir and said pumping chamber and arranged to open during the intake stroke of said pumping unit, and filter means positioned between said reservoir and said inlet check valve, said filter means including a filter element which flexes toward said inlet check valve during the intake stroke of said pumping unit to permit a predetermined amount of medication which has already passed through said filter element to flow through said inlet check valve into said pumping chamber, wherein said filter element comprises a thin back up plate of titanium having relatively large openings therein, and a woven wire mesh screen positioned adjacent said back up plate both said back up plate and said screen being sufficiently flexible to permit said predetermined amount of medication to flow through said inlet check valve into said pumping chamber.

20. The combination of claim 17, wherein during the intake stroke of said pumping unit said filter means has a pressure drop there across which is less than the minimum pressure drop required to pass a bubble of medication therethrough.

21. The combination of claim 17, wherein during the intake stroke of said pumping unit said filter means has a pressure drop of less than 0.5 psid thereacross.

22. In an implantable medication infusion unit, the combination of, a medication reservoir, a pumping chamber, a pulsatile pumping unit connected to a movable wall portion of said pumping chamber and adapted to increase the volume of said pumping chamber during the intake stroke thereof, an inlet check valve positioned between said reservoir and said pumping chamber and arranged to open during the intake stroke of said pumping unit, and filter means positioned between said reservoir and said inlet check valve to block the flow of bubbles from said reservoir and said inlet check valve to block the flow of bubbles from said reservoir to said pumping chamber, the increase in volume of the pumping chamber being greater than the volume of flow through said filter during the pump stroke, said filter means flexing during the intake stroke of said pumping unit by an amount proportional to the difference between the increase in volume of the pumping chamber and the volume of flow through the filter during the pump stroke and selected to prevent the development of a pressure drop across said filter means which is great enough to force a bubble of medication therethrough.

* * * * *